United States Patent [19]
Rosen

[11] Patent Number: 4,945,572
[45] Date of Patent: Aug. 7, 1990

[54] WELDING HELMET

[76] Inventor: Bernard Rosen, 7 Garden Ave. Brighton, Victoria 3186, Australia

[21] Appl. No.: 279,667
[22] PCT Filed: Dec. 14, 1987
[86] PCT No.: PCT/AU87/00422
 § 371 Date: Oct. 3, 1988
 § 102(e) Date: Oct. 3, 1988
[87] PCT Pub. No.: WO88/06030
 PCT Pub. Date: Aug. 25, 1988

[30] Foreign Application Priority Data

Feb. 12, 1987 [AU] Australia .................................. PI0308

[51] Int. Cl.$^5$ ................................................ A61F 9/06
[52] U.S. Cl. ........................................... 2/8; 219/147
[58] Field of Search .................... 2/8, 432, 424, 10, 9, 2/; 219/147

[56] References Cited

U.S. PATENT DOCUMENTS

| | | | |
|---|---|---|---|
| 2,036,224 | 4/1936 | Lincoln et al. | 2/8 |
| 2,904,669 | 9/1959 | Toebe | 219/147 |
| 3,153,135 | 10/1964 | Burmeister | 2/8 X |
| 3,327,317 | 6/1967 | Vattuone | 2/8 |
| 4,418,267 | 11/1983 | Pfanzelt | 219/147 |

FOREIGN PATENT DOCUMENTS

| | | |
|---|---|---|
| 120050 | 6/1943 | Australia . |
| 261265 | 12/1958 | Australia . |
| 419674 | 12/1971 | Australia . |
| 515177 | 3/1981 | Australia . |
| 0103031 | 11/1965 | Denmark ............................ 219/147 |
| 375459 | 4/1964 | Switzerland . |
| 483291 | 2/1970 | Switzerland . |
| 0245992 | 11/1969 | U.S.S.R. ................................... 2/8 |
| 666219 | 2/1952 | United Kingdom . |
| 878847 | 10/1961 | United Kingdom . |
| 959413 | 3/1964 | United Kingdom . |
| 2040118 | 8/1980 | United Kingdom ....................... 2/8 |
| 2139373 | 11/1984 | United Kingdom ................ 219/147 |

Primary Examiner—Peter Nerbun
Attorney, Agent, or Firm—Frishauf, Holtz, Goodman & Woodward

[57] ABSTRACT

A welding mask is disclosed comprising an opaque face shield having a viewing opening therein, a filter lens pivoted to the face shield adjacent the viewing opening, moving means to move the filter lens pivoted to the face shield adjacent the viewing opening, moving means to move the filter lens from a closed to an open position, said moving means including electrical transducer means to cause pivotal movement of said filter lens, restoring means to restore the filter lens to the closed position, and electrical control means for said transducer means, said control means including electrode voltage sensing means to sense the electrode voltage of an arc welder and circuit means responsive to the sensed electrode voltage to provide energy to said transducer means when the voltage rises above a predetermined maximum value and to not provide energy to the transducer when the sensed voltage falls below a predetermined minimum value.

17 Claims, 3 Drawing Sheets

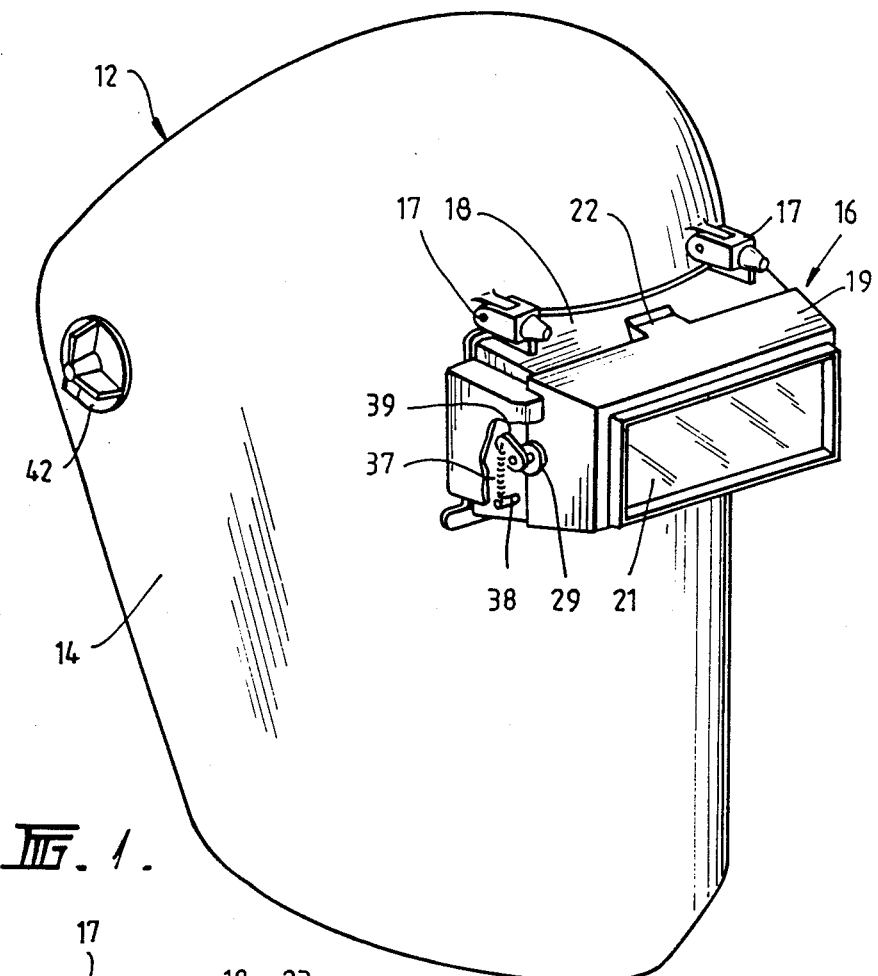
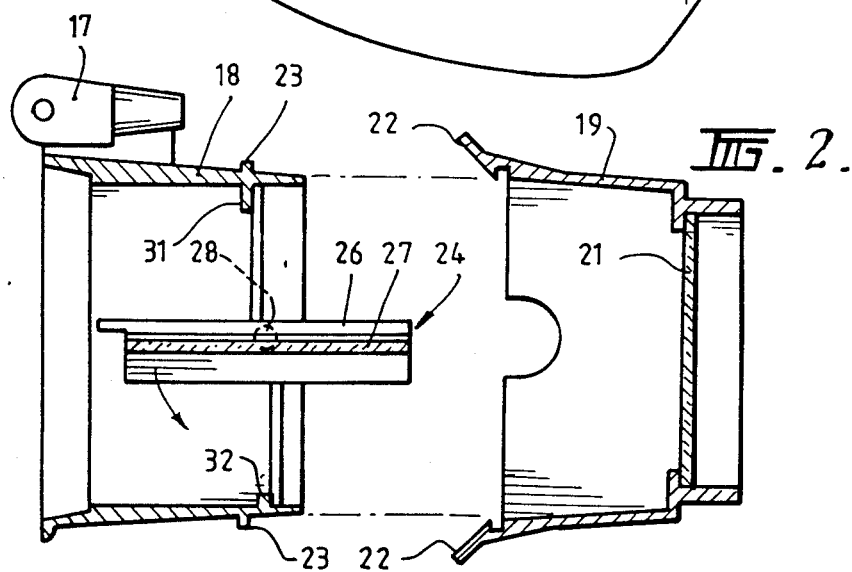

WELDING HELMET

FIELD OF THE INVENTION

This invention relates to welding masks and relates particularly to a welding mask incorporating a filter lens which is moveable between a position whereat the filter lens does not obscure a user's vision of work to be welded and an operative position in which the filter lens shields the eyes of the user from the UV light and other harmful radiation emitted during electric arc welding.

The eyes of a welder must be protected against damage from such radiation during any form of welding operation.

BACKGROUND OF THE INVENTION

It has been the practice to provide either a hand held welding mask having a filter lens formed of a darkened window which is moved in front of the eyes on commencement of welding or a mask which is worn by the welder and which is generally moveable between an operative position at which the welder looks through the filter lens and an inoperative position at which the mask is tilted back on the head of the user or the filter lens moved on a pivot allowing clear vision of the work.

Such masks, however, are unsafe due to the tendency of the user to strike an arc before the mask is properly in place, thus subjecting the user's eyes to the damaging radiation. The problem is accentuated when welding is carried out in conditions of poor light where it is impossible for the welder to see the work through the filter lens before the arc is struck.

The problem of eye damage caused by the radiation emitted from a welding arc has dramatically increased with the increasing use of hobby arc welders which are now commonly available and used by amateur welders without any formal training or experience. However, the problem also exists for trained and experienced welders who can accidentally be exposed to the radiation.

BACKGROUND ART

It has been proposed to provide welding masks with a filter lens which becomes darkened or opaque in the presence of UV and other radiation but which clarifies in the absence of such radiation. However, the time taken for such a lens to become opaque is such that some radiation can impinge on the eyes of a user.

Australian Pat. No. 515,177 discloses a hand held mask having a trigger which actuates a hinged filter lens mechanism and a light switch. When the trigger is actuated, the filter lens swings out of the line of vision of the user to enable the work to be viewed. Greater trigger pressure actuates the light switch to cause the work to be illuminated by the self-contained light. On release of the trigger, the filter lens swings back into the shielding position.

With this construction, it is possible for the user to strike an arc while the filter lens is out of the line of vision so that the user is subjected to radiation.

Australian Pat. No. 419,674 discloses another construction of mask in which a moveable opaque filter lens is pivoted along it's upper edge and is moveable by a lever mechanism operable by the chin of the user to open or close the filter lens. Again, correct operation of this mask depends on proper actuation by the user.

Other similar devices have been shown in Australian Pat. specification Nos. 120,050 and 261,265.

It is, therefor, desirable to provide an improved construction of welding mask whereby the filter lens does not obscure, or substantially obscure, vision of the work when there is no arc but which protects the eyes of the user against radiation when an arc is struck.

It also desirable to provide an improved welding mask which is able to be used with a variety of arc welding equipment.

It is also desirable to provide an improved welding mask which is effective in automatically preventing radiation reaching the eyes of a user but which enables the user to clearly see the work and leaves one hand free to position the work piece to be welded or to hold on to a support in hazardous locations.

It is also desirable to provide a welding mask which has the above features and which is also economical to manufacture.

SUMMARY OF THE INVENTION

According to the invention there is provided a welding mask comprising an opaque face shield having a viewing opening therein, a filter lens pivoted to the face shield adjacent the viewing opening, moving means to move the filter lens from a closed to an open position, said moving means including electrical transducer means to cause pivotal movement of said filter lens, restoring means to restore the filter lens to the closed position, and electrical control means for said transducer means, said control means including electrode voltage sensing means to sense the electrode voltage of an arc welder and circuit means responsive to the sensed electrode voltage to energise said transducer means when the voltage rises above a predetermined maximum value and to de-energise the transducer when the sensed voltage falls below a predetermined minimum value.

Preferably, the mask is of the face shield type adapted to be worn on the head, although it will be appreciated that the invention is applicable to hand held shields.

In a preferred form of the invention, the filter lens is pivotally mounted on a frame forming part of or attached to the face shield. The pivotal axis of the lens is generally horizontal and passes either through the centre of gravity of the lens or adjacent thereto. With this arrangement, the operation of the transducer acts to pivot the lens about its axis of symmetry, thus requiring less operational forces as compared to physically moving the lens away from the viewing opening. In the open position, the filter lens is substantially centrally located in the viewing area but extends perpendicular thereto so that the user can look past the lens to the work.

In a preferred form of the invention, the transducer means comprises a solenoid mounted on the face shield and connected by a crank lever to the lens pivot shaft. The restoring means comprises a tension spring which is also connected by a crank lever to the lens pivot shaft and which also constitutes part of the circuit means. With this arrangement, if the spring fails, no current will flow to the solenoid and the filter lens will remain in a closed position.

The welding mask of the invention can be designed for a standard electric arc welder which has an operating voltage in the range of 50 to 80 volts a.c. between the welding electrode and the work. When the arc is struck, the voltage across the arc drops by approximately 50 percent.

In an alternative embodiment, the welding mask is designed for use with a standard rod arc welder, a MIG, an a.c. TIG or a d.c. TIG. In this embodiment, a switch is provided, preferably mounted on the face shield or lens frame, to enable the user to switch the electrical control means to suit the particular welder in use. Thus, in the normal MIG and TIG type welders, direct current is normally employed and the welder is operated by a switch mounted on the electrode holder. For this embodiment, the control circuit must take account of both a.c. and d.c. electrode voltages as well as the polarity differences between MIG and TIG d.c. welders.

The invention will be more readily understood by reference to the following description of embodiments of the invention taken in conjunction with the accompanying drawings.

DESCRIPTION OF THE DRAWINGS

FIG. 1 is a perspective view, part cut away, showing a welding mask in accordance with one embodiment of the present invention, FIG. 2 is a sectional, side elevational view showing the filter lens frame and cover therefor.

DESCRIPTION OF THE PREFERRED EMBODIMENTS

Figure 3:
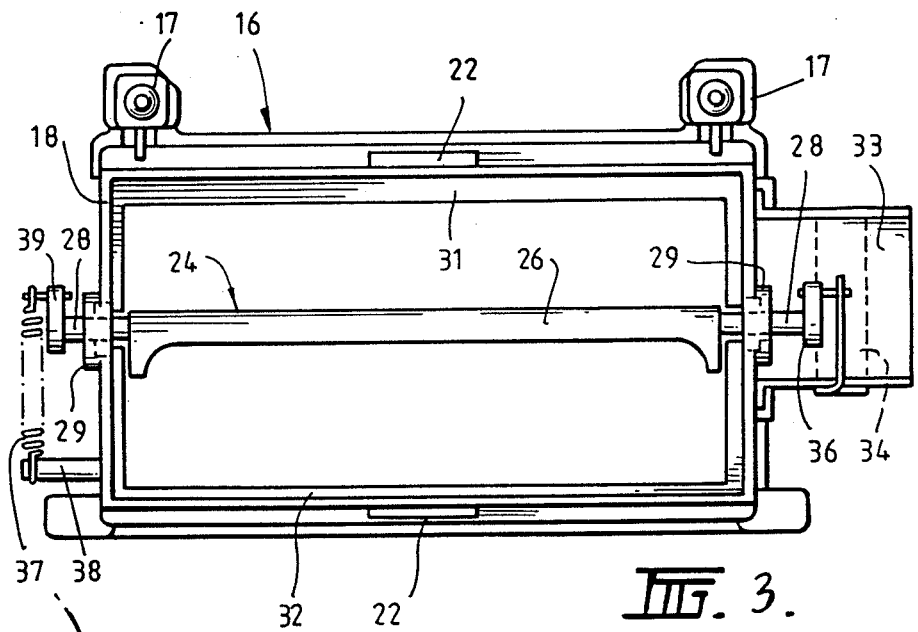
FIG. 3 is a front elevational view of the filter lens and mounting frame.
Figure 4:
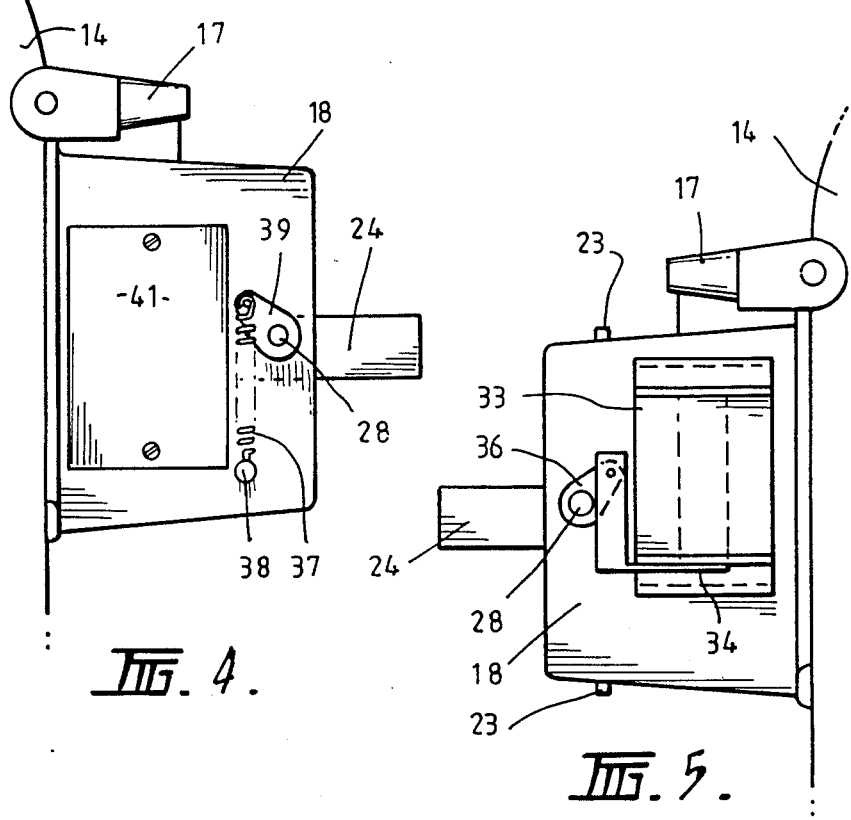
FIG. 4 is one side elevational view of the filter lens frame.
Figure 5:
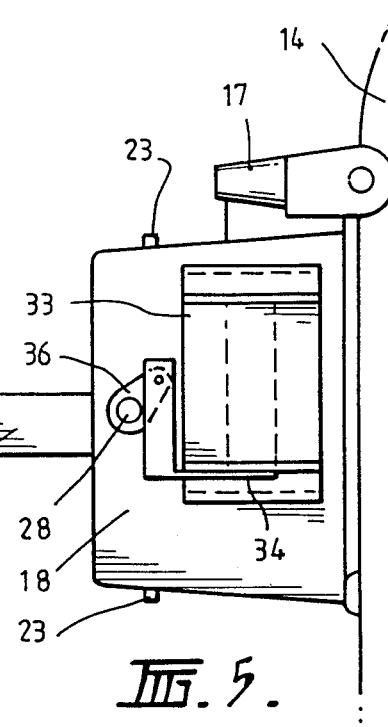
FIG. 5 is a side elevational view of the filter lens frame taken from the opposite side to that of FIG. 4.

FIGS. 1 to 5 illustrate a welding mask 12 which comprises a face shield 14 and a lens frame 16 mounted to the face shield 14 by mounting brackets 17. The face shield 14 has an internal head band (not shown) enabling the face shield to be worn by a welder.

The lens frame 16 projects from the face shield 14 and includes an inner frame part 18 and a cover 19. The cover 19 has a clear glass or glass-like protective front 21 and upper and lower clips 22 which are adapted to engage upstanding ribs 23 on the inner frame part 18. Thus, the cover 19 is removeable from the inner frame part 18 to provide access to the filter lens 24 which is mounted on the inner frame part 18.

The filter lens 24 includes a lens holder 26 which releaseably carries the filter lens glass 27, thus permitting easy replacement, if required. The lens holder 26 is provided with opposed outwardly extending pivot axles 28 which extend through bearings 29 on each side of the inner frame part 18. The axis of the pivot axles 28 is substantially horizontal in normal use of the welding mask 12 and is located slightly offset from the axis through the centre of balance of the filter lens 24 so that the lens 24 normally lies in a vertical plane.

The inner frame part 18 is provided with upper and lower stops 31 and 32 against which the filter lens 24 engages when moved to the vertical, closed position A solenoid 33 is mounted on one side of the lens frame 16. The solenoid plunger 34 is connected by a crank 36 to one of the pivot axles 28 so that vertical movement of the plunger 34 causes rotational movement of the filter lens 24. On the opposite side of the lens frame 16, a spring 37 engaged on a pin 38 extending from the lens frame 16 is connected to a second crank 39 fixed to the other of the pivot axles. 28 The spring acts to move the filter lens 24 about the pivot axis to the closed position.

The solenoid 33 is actuated through a control circuit, components of which are mounted on a printed circuit board 41 mounted on one side of the lens frame 16. The control circuit may be that illustrated in FIG. 6, in which case the welding mask 12 is able to be used only with a normal, a.c. arc welder. Alternatively, the control circuit may be that illustrated in FIG. 7, in which case the welding mask 12 includes a change-over switch 42 which enables the circuit to be switched to suit the various types of arc welders.

Figure 6:
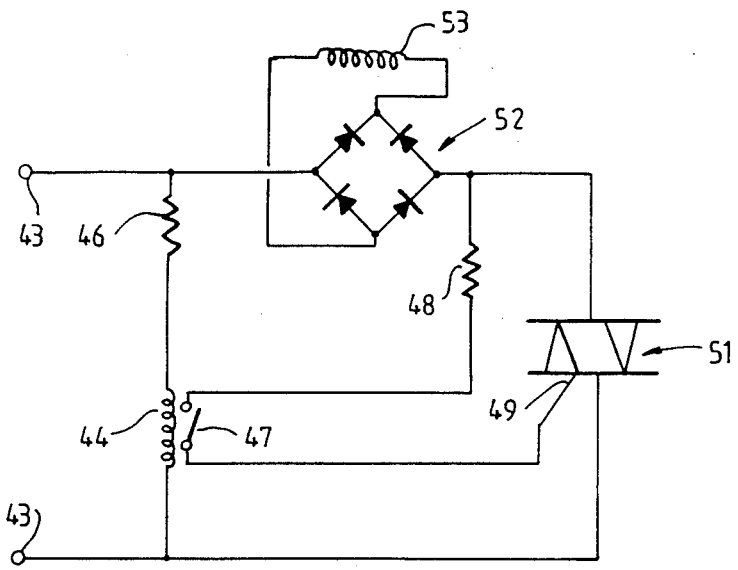
FIG. 6 is a circuit diagram illustrating a control circuit for a standard electric arc welder.

Referring to FIG. 6, the control circuit illustrated is suited for a normal, a.c. arc welder. The circuit includes inputs 43, one of which is connected to the welding electrode while the other of which is connected to the work. A reed switch coil 44 is connected inputs 43 in series with a voltage dropping resistor 46, the series combination is connected across inputs 43. The reed switch coil has.. an operating voltage of approximately 10 volts and the resistor 46 is selected so that a voltage of between 50 and 80 volts a.c. across the inputs 43, which corresponds to the open circuit electrode to work voltage, causes operation of the reed switch 47. The switch 47 connects the resistor 48 to the gate 49 of the triac 51 causing the triac to conduct and thus closing the circuit to the bridge rectifier 52. The bridge rectifier rectifies the input voltage and applies this to the solenoid coil 53 The coil is therefore energised and the plunger 34 of the solenoid 33 holds the filter lens 24 in the open position as shown in FIG. 2.

As soon as the welding electrode contacts the work in order to strike an arc, the voltage across inputs 43 drops below a level at which the reed switch coil 44 will hold the reed switch 47 closed The gate 49 is, thus, open circuited and the triac 51 immediately ceases to conduct, thereby open circuiting the solenoid coil 53. The restoring spring 37 immediately acts to rotate the filter lens 24 about the pivot axis to the closed position at which position radiation from the welding arc is prevented from damaging the eyes of the welder.

Immediately the arc is broken, the voltage between the electrode and the work increases, causing the reed switch coil 44 to close the reed switch 47 thus actuating the solenoid coil 53 to open the filter lens 24.

Figure 7:
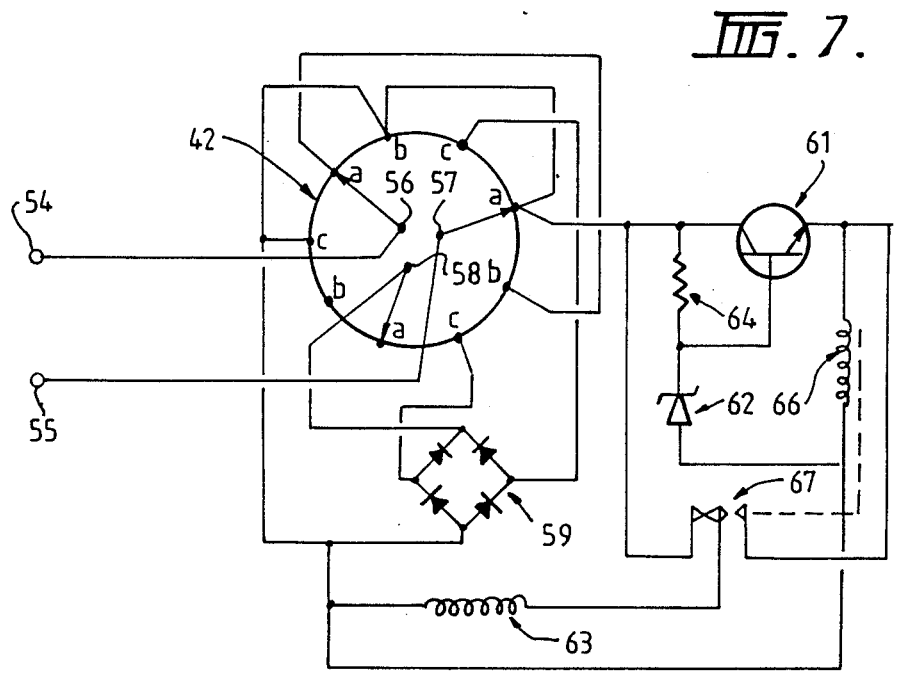
FIG. 7 is a circuit diagram illustrating a control circuit for a welding mask for use with different types of arc welders.

The circuit illustrated in FIG. 7 includes a change over switch 42 which enables the circuit to be used for the various types of electric arc welders. The change over switch 42 is a 3 pole, 3 way switch to enable the control circuit to take account of the input voltage being a.c. or either polarity of d.c. Referring to FIG. 7, the input 54 is connected to the work while the input 55 is connected to the anode. The inputs are connected to switch poles 56 and 57, respectively. The switch poles 56/57/58 can be switched between positions a,b and c which correspond to MIG, TIG a.c. and TIG d.c. respectively The switch is shown in FIG. 7 at position a. As will be seen, the difference between MIG and TIG d.c. positions is simply a reversal of polarity.

The input voltage (in the case of TIG a.c., rectified by the bridge rectifier 59) is applied to the voltage regulator circuit incorporating transistor 61 the zener diode 62. While the voltage is higher than the zener voltage, the transistor 61 conducts, thus energising the solenoid col 63. As soon as the voltage across the inputs drops due to the contact of the electrode with the work, the transistor ceases to conduct and the coil is open circuited causing the spring 37 to close the filter lens 24.

In the preferred embodiment illustrated in FIG. 7, the transistor is an npn type 2N3055 while the zener diode is a 12 volt diode with the biasing resistor 64 preferably 150 ohms.

A relay coil 66 is connected across the transistor 61 and actuates a single pole, double throw relay switch 67. Thus, if any of the circuit components such as the zener diode 62 or transistor 61 malfunction, the relay actuates to open circuit the solenoid coil 63 causing the filter lens 24 to be moved to the closed, or safe, position.

In the preferred embodiments of the invention, the spring 37 is preferably part of the electrical circuit to solenoid 33 so that, in the event of the spring failing, the solenoid cannot be energized to open the filter lens 24.

It has been found that with the welding mask of the embodiments described, when the welding electrode touches the work prior to striking the arc, the lens closes within approximately 3 milliseconds. This time is generally less than the time required to actually strike the arc. Further, as soon as the arc breaks, the lens opens at a slower rate than the closing rate, and any subsequent contact of the electrode with the work causes the lens to re-close within the 3 millisecond period. Similar times are applicable to MIG and TIG welders using switch controls.

In claim:

1. A welding mask, comprising:
   a face shield having a viewing opening therein;
   a filter lens pivotally mounted relative to said face shield adjacent to said viewing opening;
   solenoid means for moving said filter lens from a closed position to an open position;
   pivoting means coupled to said solenoid means for pivoting said filter lens about an axis which passes either through the center of said filter lens or adjacent thereof;
   restoring means for restoring said filter lens to the closed position;
   electrical control means for controlling said solenoid means, said electrical control means including:
   electrode voltage sensing means for sensing an electrode voltage on an electric arc welder;
   circuit means responsive to a sensed electrode voltage for operating said solenoid means when the sensed electrode voltage rises above a predetermined maximum value, and for deactivating said solenoid means when the sensed electrode voltage falls below a predetermined minimum value for enabling said restoring means to move said filter lens from said open position to said closed position;
   voltage input terminal means for connecting to a welder electrode and the work for receiving the voltage therebetween;
   a reed switch and a reed switch coil associated therewith, said reed switch being held in a closed position when a voltage across said reed switch coil is above said predetermined maximum value;
   a triac having a gate which is connected in a circuit with said reed switch and which is held on while said reed switch is closed to energize said solenoid means through a bridge rectifier, said reed switch open-circuiting said triac gate when said electrode voltage falls below said predetermined minimum value.

2. A welding mask according to claim 1, wherein said restoring means comprises at least one spring means.

3. A welding mask according to claim 2, wherein said spring means comprises part of said circuit means such that if said spring means breaks the circuit means is rendered open circuited.

4. A welding mask according to claim 2, wherein said pivoting means comprises a crank lever means.

5. A welding mask according to claim 1, wherein said filter lens is pivotally mounted on a frame forming part of said face shield, said filter lens having a pivotal axis which passes adjacent to the center of said filter lens such that, when said filter lens is in said open position, said filter lens is substantially centrally located in a viewing area and substantially perpendicular thereto, but moves under a gravity force to the closed position in the absence of any opening force.

6. A welding mask according to claim 1, wherein said filter lens is pivotally mounted on a frame coupled to said face shield, said filter lens having a pivotal axis which passes adjacent to the center of said filter lens such that, when said filter lens is in said open position, said filter lens is substantially centrally located in a viewing area and substantially perpendicular thereto, but moves under a gravity force to the closed position in the absence of any opening force.

7. A welding mask, comprising:
   a face shield having a viewing opening therein;
   a filter lens pivotally mounted relative to said face shield adjacent the viewing opening;
   moving means for moving said filter lens from a closed position to an open position;
   said moving means including electrical transducer means for causing a pivotal movement of said filter lens;
   restoring means for restoring said filter lens to the closed position; and
   electrical control means for controlling said transducer means;
   said electrical control means including:
   electrode voltage sensing means for sensing an electrode voltage of an electric arc welder;
   circuit means responsive to the sensed electrode voltage for operating said transducer means when the sensed electrode voltage rises above a predetermined maximum value, and for deactivating said transducer means when the sensed electrode voltage falls below a predetermined minimum value for enabling said restoring means to move said filter lens from said open position to said closed position;
   control switch means including a 3-pole, 3-way control switch which includes voltage input terminals for connecting to a welding anode and the work; and
   a voltage regulator circuit including a transistor controlled by a zener diode for switching on the transistor to energize said transducer means when the voltage across the zener diode is greater than said predetermined maximum value and to turn off the transistor when the voltage falls below the zener voltage;
   said control switch means further including means for enabling said control circuit to operate with an a.c. input voltage or a d.c. voltage of either polarity.

8. A welding mask according to claim 7, further comprising a safety cutout means coupled to said transducer means for de-energizing said transducer means in the event of a failure of said zener diode.

9. A welding means according to claim 8, wherein said transducer mean s comprises a solenoid for causing said pivotal movement of said filter lens.

10. A welding mask according to claim 7, further comprising a safety cutout means coupled to said transducer means for de-energizing said transducer means in the event of a failure of said transistor.

11. A welding means according to claim 10, wherein said transducer means comprises a solenoid for causing said pivotal movement of said filter lens.

12. A welding mask according to claim 7, wherein said transducer means comprises a solenoid for causing said pivotal movement of said filter lens.

13. A welding means according to claim 7, wherein said control switch is mounted on said face shield.

14. A welding mask according to claim 7, wherein said restoring means comprises at least one spring means.

15. A welding mask according to claim 12, wherein said spring means comprises part of said circuit means such that if said spring means breaks the circuit means is rendered open circuited.

16. A welding mask according to claim 7, wherein said filter lens is pivotally mounted on a frame forming part of said face shield, said filter lens having a pivotal axis which passes adjacent to the center of said filter lens such that, when said filter lens is in said open position, said filter lens is substantially centrally located in a viewing area and substantially perpendicular thereto, but moves under a gravity force to the closed position in the absence of any opening force.

17. A welding mask according to claim 7, wherein said filter lens is pivotally mounted on a frame coupled to said face shield, said filter lens having a pivotal axis which passes adjacent to the center of said filter lens such that, when said filter lens is in said open position, said filter lens is substantially centrally located in a viewing area and substantially perpendicular thereto, but moves under a gravity force to the closed position in the absence of any opening force.

* * * * *